(12) United States Patent
Nam et al.

(10) Patent No.: US 9,387,104 B2
(45) Date of Patent: Jul. 12, 2016

(54) LOADING BASKET FOR A STENT DELIVERY SYSTEM

(75) Inventors: Ra Nam, Lawrence, MA (US); Mark Wood, Shrewsbury, MA (US); John Pereira, Brighton, MA (US); Eric M. Schneider, Lincoln, RI (US); William C. Bertolino, Framingham, MA (US); Naroun Suon, Lawrence, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 902 days.

(21) Appl. No.: 13/335,615

(22) Filed: Dec. 22, 2011

(65) Prior Publication Data
US 2012/0172962 A1    Jul. 5, 2012

Related U.S. Application Data

(60) Provisional application No. 61/428,836, filed on Dec. 30, 2010.

(51) Int. Cl.
*A61F 2/06* (2013.01)
*A61F 2/962* (2013.01)
*A61F 2/95* (2013.01)

(52) U.S. Cl.
CPC ......... *A61F 2/962* (2013.01); *A61F 2002/9522* (2013.01)

(58) Field of Classification Search
CPC . A61F 2/962; A61F 2/966; A61F 2002/9522; A61F 2/95; A61F 2/954; A61F 2002/9583
USPC .......................................... 623/1.11; 606/200
See application file for complete search history.

(56) References Cited

U.S. PATENT DOCUMENTS

| | | | |
|---|---|---|---|
| 5,100,422 A | | 3/1992 | Berguer et al. |
| 5,387,235 A | * | 2/1995 | Chuter ................ 623/1.11 |
| 5,683,451 A | * | 11/1997 | Lenker et al. .............. 623/1.11 |
| 5,755,769 A | * | 5/1998 | Richard et al. ................ 623/1.2 |
| 6,679,902 B1 | * | 1/2004 | Boyle .................... A61F 2/95 606/200 |
| 7,303,580 B2 | * | 12/2007 | Parker ..................... 623/1.11 |
| 7,670,364 B2 | | 3/2010 | Dusbabek et al. |
| 2002/0058963 A1 | * | 5/2002 | Vale et al. ................. 606/200 |
| 2007/0270932 A1 | | 11/2007 | Headley et al. |
| 2009/0192518 A1 | * | 7/2009 | Golden .................. A61F 2/95 606/108 |
| 2010/0137846 A1 | * | 6/2010 | Desai .................. A61B 17/221 606/2.5 |

FOREIGN PATENT DOCUMENTS

| | | |
|---|---|---|
| WO | 00/71059 | 11/2000 |
| WO | 2008/031103 | 3/2008 |

* cited by examiner

*Primary Examiner* — Diane Yabut
*Assistant Examiner* — Martin T Ton
(74) *Attorney, Agent, or Firm* — Seager, Tufte & Wickhem, LLP

(57) ABSTRACT

A loading basket is secured at its proximal end to a portion of a delivery device. The stent engages with the interior of the stent basket when loaded onto the delivery device to prevent shifting or movement of the stent during delivery of the stent to a desired location within the bodily lumen. In at least one embodiment, the loading basket has a proximal end, a distal end, and a braided surface. The loading basket comprises a proximal end portion, a proximal transition portion, a body portion, a distal transition portion, a distal end portion, and an angled inward distal end. When loaded onto the delivery device, the outer surface of the stent contacts at least the angled inward distal end of the delivery device and movement of the stent is prevented.

20 Claims, 9 Drawing Sheets

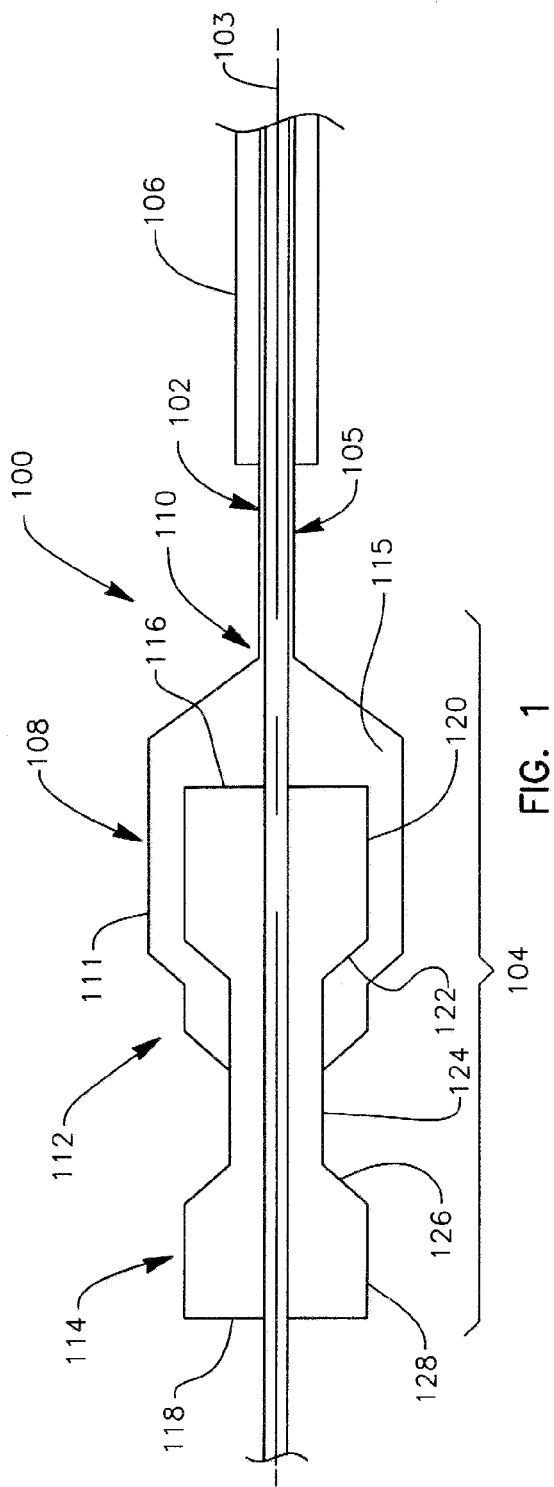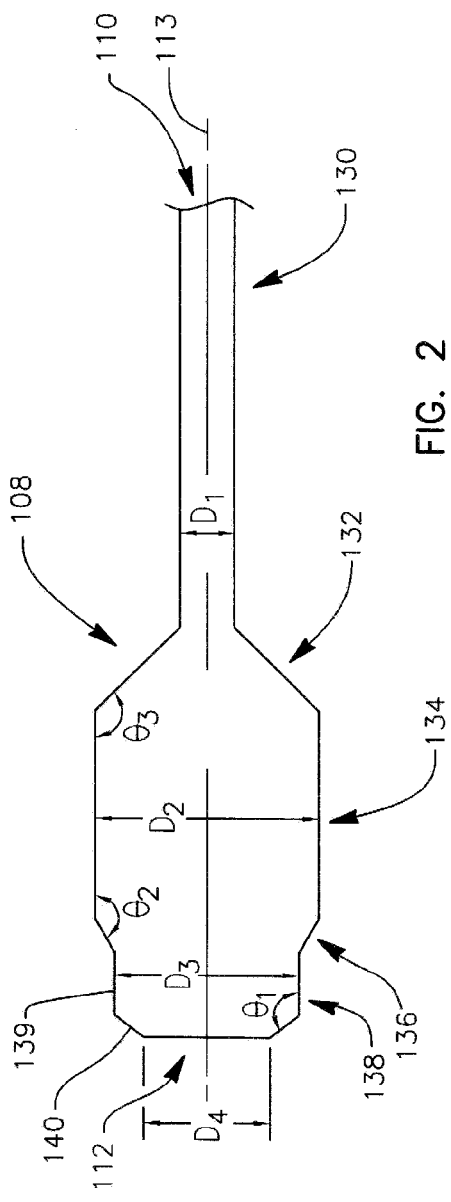
FIG. 1
FIG. 2

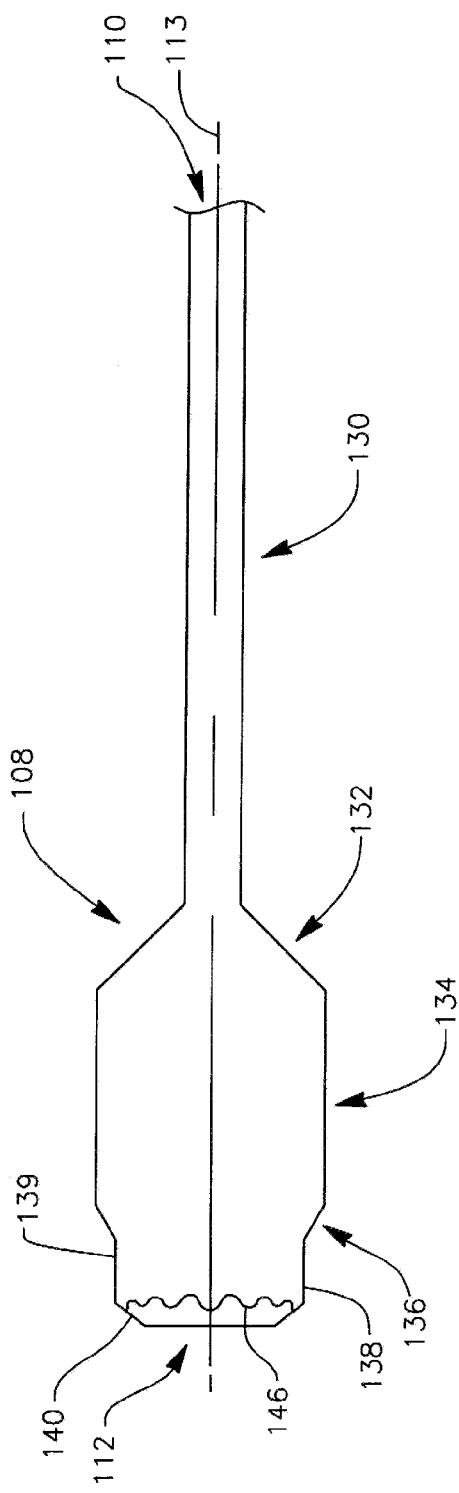
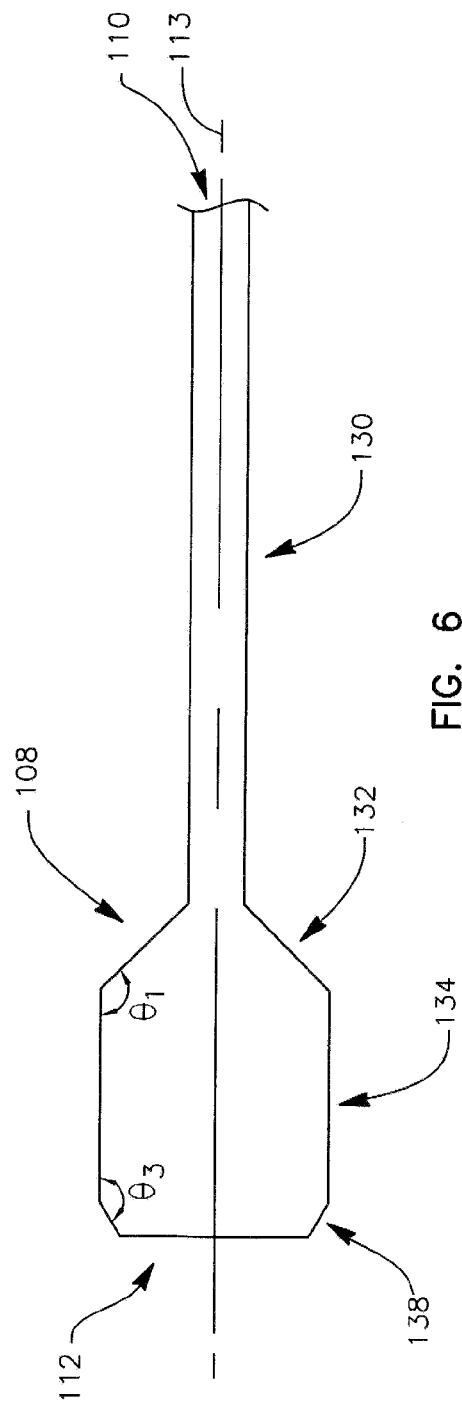
FIG. 5
FIG. 6

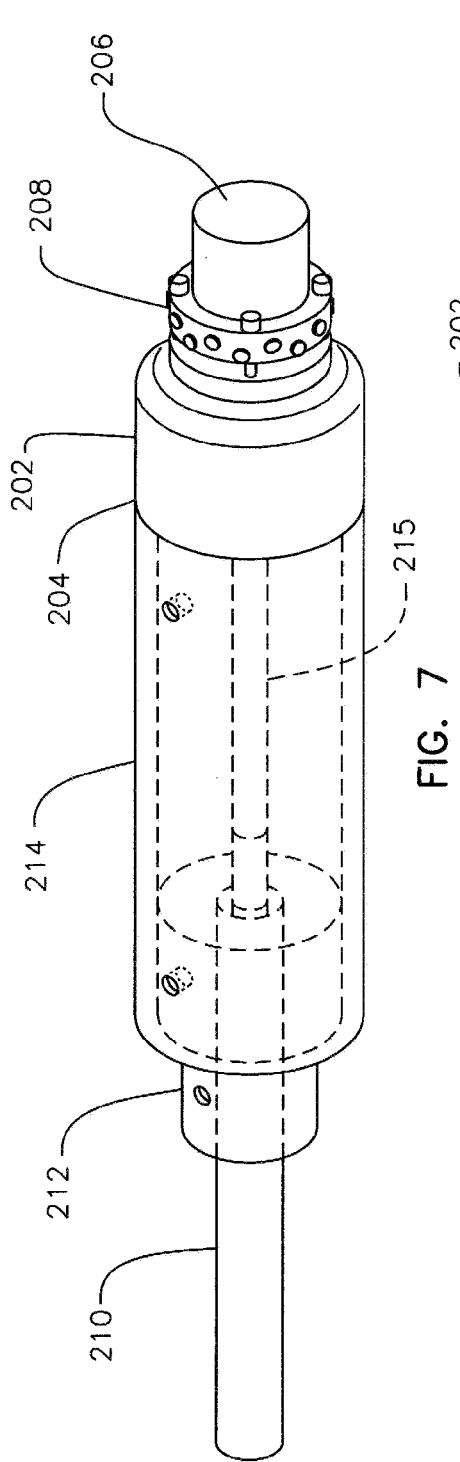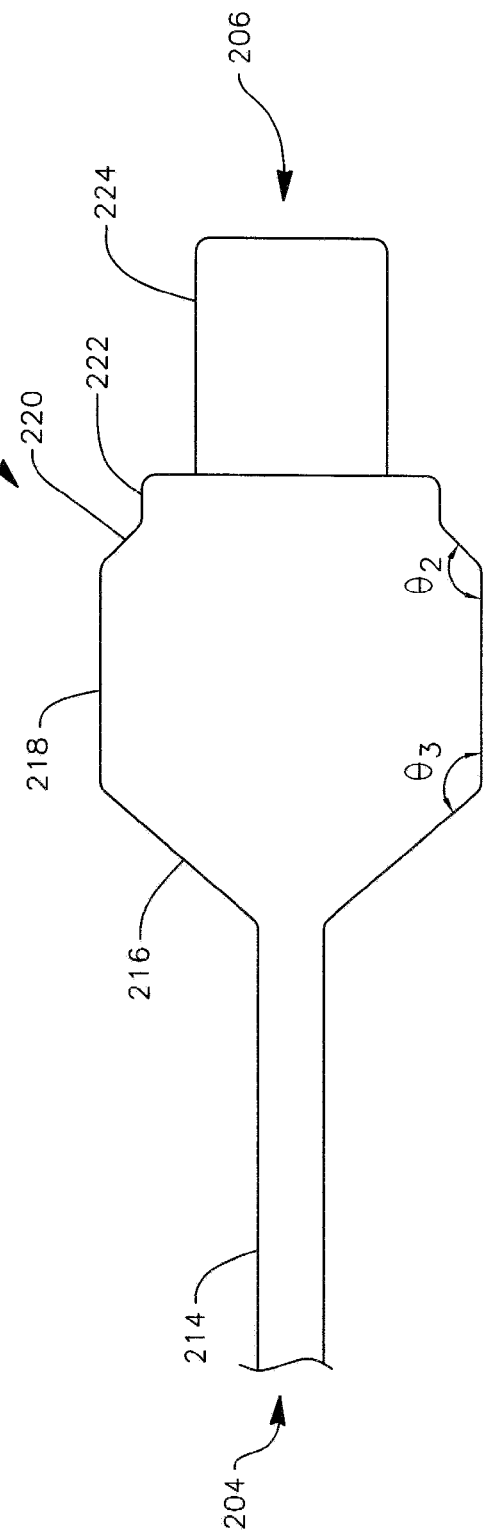
FIG. 7
FIG. 8

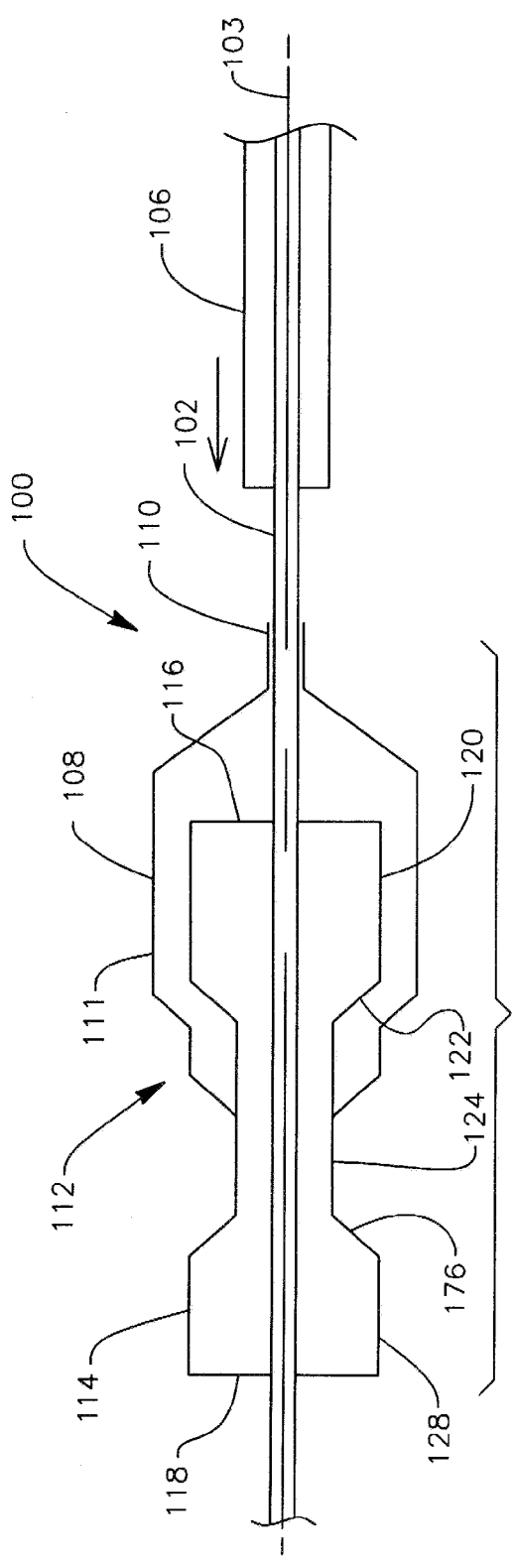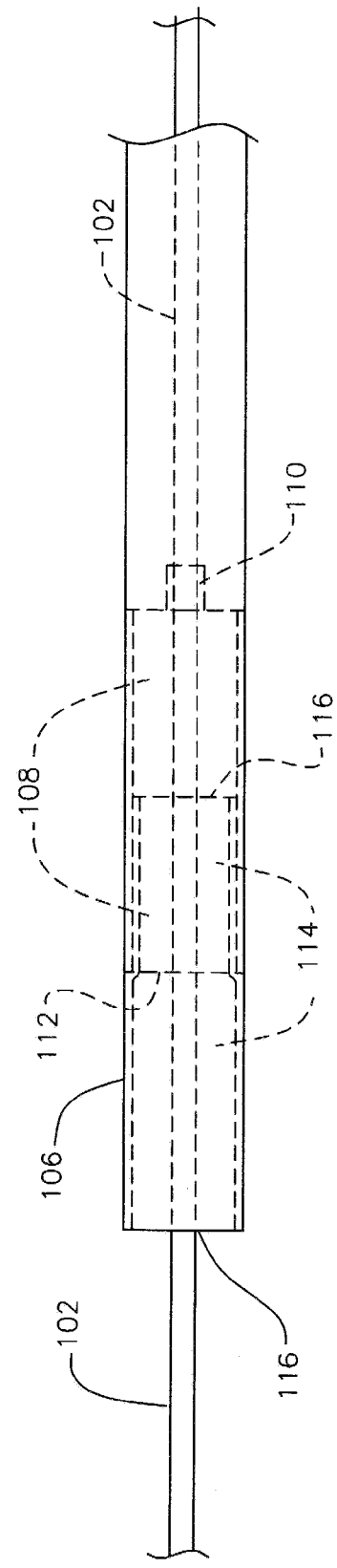
FIG. 11B
FIG. 11C

LOADING BASKET FOR A STENT DELIVERY SYSTEM

CROSS REFERENCE TO RELATED APPLICATIONS

This application claims the benefit of U.S. Provisional Application No. 61/428,836, filed Dec. 30, 2010, the contents of which is hereby incorporated by reference.

BACKGROUND OF THE INVENTION

This invention relates generally to a delivery system for medical devices such as stents. More particularly, the invention relates to a loading basket for a stent delivery system and methods of manufacturing the loading basket.

Medical devices such as stents and other intraluminary prostheses are used in the repair and/or treatment of diseases in various body vessels. A stent is generally a longitudinal tubular device formed of biocompatible materials useful to open and support various lumens in the body. For example, stents may be used in bodily vessels, such as the coronary or peripheral vasculature, esophagus, trachea, bronchi, colon, biliary tract, urinary tract, prostate, brain, and other vessels. These devices are implanted within the vessel to open and/or reinforce collapsing or partially occluded sections of the lumen. Stents radially expand to support and reinforce the bodily vessel, and can be self-expanding and/or or mechanically expandable using balloons and other means to expand the stent.

The stent delivery system typically includes a catheter assembly to properly position the stent in the vessel and deploy the stent. The catheter assembly retains the stent in a radially compressed configuration while the stent is advanced to the desired location in the vessel, and then allows the stent to radially expand. The catheter assembly may include balloons, sheaths, and other structures used to maintain the stent in a radially compressed configuration and radially expand the stent during deployment.

Although stent delivery systems are well-known in the art, the assembly of such delivery systems is often complicated. In some instances, stents are loaded by a practitioner into the stent delivery system shortly before being implanted in a patient. However, this loading process often involves numerous steps and requires the use of multiple tools and fixtures that are not part of the stent delivery system. The practitioner is often required to finish the loading process by pushing the stent into the delivery system by hand. It is important that the stent be loaded at the proper position on the catheter to ensure proper deployment and expansion of the stent.

As described in co-owned US Pat. Publication No. 2009/0192518, which is incorporated by reference herein in its entirety, stent delivery systems sometimes use a loading basket secured to a portion of a delivery device.

The art referred to and/or described above is not intended to constitute an admission that any patent, publication or other information referred to herein is "prior art" with respect to this invention. All U.S. patents and applications and all other published documents mentioned anywhere in this application are incorporated herein by reference in their entirety.

BRIEF SUMMARY OF THE INVENTION

In at least one embodiment of the present invention, the loading basket has a proximal end, a distal end, and a braided surface. The loading basket comprises a proximal end portion, a proximal transition portion, a body portion, a distal transition portion, and a distal end portion having a first section and a second section. In at least one embodiment, the first section has a constant diameter and the second section has a diameter that tapers from the constant diameter of the first section to a diameter that is less than the constant diameter of the first section. In some embodiments, the loading basket further comprises a gripper region between the distal transition portion and the distal end portion. In at least one embodiment, the gripper region has a diameter that is smaller than the diameter of the distal end portion.

A stent delivery system is also provided and has a loaded state and a deployed state. In at least one embodiment, the stent delivery system comprises an elongated inner member having a stent loading region, an intermediate tubular member slidably engaged with the inner member, and an outer tubular member slidably engaged with the intermediate tubular member. In one embodiment, a loading basket has a proximal end and a distal end, where the proximal end is secured to a distal end of the intermediate tubular member. In at least one embodiment, the proximal end of the stent is deposited within an inner surface of the loading basket and extending therefrom at the stent loading region. The stent engages with the interior of the loading basket when loaded onto the delivery device to prevent shifting or movement of the stent during delivery of the stent to a desired location within the bodily lumen.

In some embodiments, in the loaded state, the distal end of the loading basket contacts an outer surface of the stent. In some embodiments, in the loaded state, the outer tubular member slides over the loading basket and the stent to radially compress the loading basket and the stent. In some embodiments, in the deployed state, the outer tubular member and the intermediate tubular member are retracted to allow the stent and the loading basket to radially expand and deploy the stent. In some embodiments, the inner shaft, along with the attached loading basket, is withdrawn.

A method of manufacturing the loading basket is also provided. The loading basket can be laser cut from a material or can be braided, twisted, knotted, knitted, woven, braided, bent, twisted, knotted, laser cut, molded, tied, and/or wrapped from one or several filaments into a desired configuration. In at least one embodiment, the loading basket is braided from a monofilament wire using a braiding machine having a mandrel assembly. In at least one embodiment, the mandrel assembly comprises a mandrel having a proximal end portion, a proximal transition portion, a body portion, a distal transition portion, and a distal end portion. In some embodiments, the mandrel further comprises a gripping region between the distal transition portion and the distal end portion. In at least one embodiment, the mandrel assembly further comprises a removable tube. In some embodiments, the mandrel assembly further comprises a removable hook end assembly.

In at least one embodiment, a method of loading a stent onto a stent delivery system and delivering the stent therefrom is provided. In at least one embodiment, the stent delivery system has a loading basket attached to a first tubular member at a stent loading region. In at least one embodiment, a proximal end of the stent is inserted into a body of the loading basket, such that an outer surface of the stent contacts an inner surface of the loading basket. In at least one embodiment, a second tubular member is slid over both the loading basket and the stent such that both are radially compressed. In at least one embodiment, the stent delivery system is advanced to a desired location in a bodily vessel. In at least one embodiment, at least the second tubular member is retracted to radially expand the stent that is held within the loading basket, thus deploying the stent. In at least one embodiment, the first tubular member having the loading basket, and the second tubular member are retracted from the lumen, leaving the deployed stent in the desired location in the lumen.

BRIEF DESCRIPTION OF THE SEVERAL VIEWS OF THE DRAWING(S)

FIG. 1 shows a cross-sectional view of the stent delivery system of the present invention.

FIG. 2 shows a cross-sectional view of an embodiment of the loading basket of the present invention.

FIG. 5 shows a cross-sectional view of an embodiment of the loading basket of the present invention.

FIG. 6 shows a cross-sectional view of an embodiment of the loading basket of the present invention.

FIG. 7 shows a perspective view of an embodiment of the mandrel assembly used to form the loading basket of the present invention.

FIG. 8 shows a cross-sectional view of an embodiment of the mandrel.

FIGS. 11A-11D show the method of loading and deploying the stent using the stent delivery system of the present invention.

DETAILED DESCRIPTION OF THE INVENTION

Figure 3:
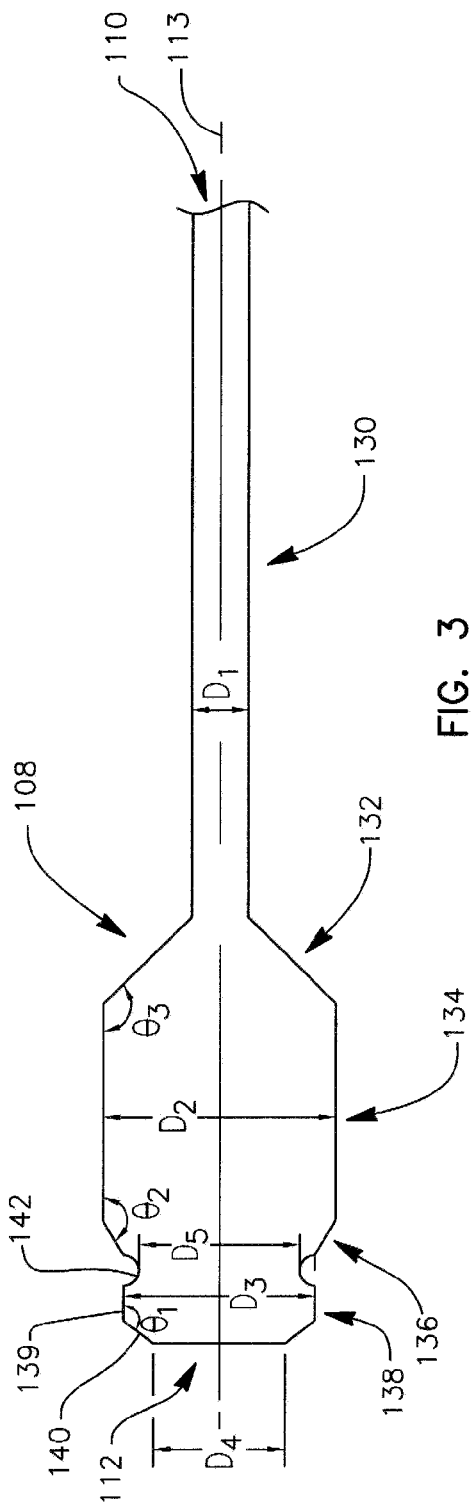
FIG. 3 shows a cross-sectional view of an embodiment of the loading basket of the present invention.

FIG. 1 shows a stent delivery system 100 of the present invention comprising a first elongated member 102 with a longitudinal axis 103 and a stent loading region 104; an intermediate tubular member 105 slidably engaged with the inner elongated member 102; and an outer tubular member 106 slidably engaged with the intermediate tubular member 105. In at least one embodiment, the first elongated member 102 is coaxial with the intermediate tubular member 105, which is coaxial with the outer tubular member 106.

A loading basket 108 is attached to the intermediate tubular member 105. The loading basket 108 has a proximal end 110, a distal end 112, and a surface 111 extending from proximal end 110 to distal end 112 that defines an inner lumen 115. In at least one embodiment, surface 111 is a braided surface. The proximal end 110 is attached to the intermediate tubular member 105 at a distal end of the intermediate tubular member.

A stent 114 having a proximal end 116 and a distal end 118 is loaded onto the stent delivery system 100 at the stent loading region 104 and is retained within the inner lumen 115 of the loading basket 108. In at least one embodiment, the stent 114 contacts the braided surface 111 of the loading basket 108. In at least one embodiment, the distal end 112 of the loading basket 108 contacts the stent 114. In some embodiments, the stent 114 has a constant diameter along a length of the stent. In other embodiments, the stent 114 has a non-constant diameter along the length of the stent. In at least one embodiment, stent 114 is a flared stent having a proximal flared section 120, proximal transition section 122, body section 124, distal transition section 126 and distal flared section 128.

Although FIG. 1 shows the delivery system has having three members, with the loading basket attached to the intermediate tubular member, in at least one embodiment the loading basket can be attached to the innermost member (for example, inner elongated member 102).

FIG. 2 shows an embodiment of the loading basket 108 having a proximal end 110, a distal end 112, and a longitudinal axis 113 extending therebetween. In the embodiment shown, the loading basket 108 has essentially a stepped configuration. The loading basket 108 comprises a proximal end portion 130, a proximal transition portion 132, a body portion 134, a distal transition portion 136, and a distal end portion 138. In at least one embodiment, the distal end portion 138 has a first section 139 axially adjacent to the distal transition portion and a second section 140 axially adjacent to the first section 139. In at least one embodiment, the second section 140 has a plurality of loops 141 that form the distal end 112 of the loading basket 108. In at least one embodiment, the second section 140 of the distal end portion 138 is angled toward the longitudinal axis 113 relative to the first section 139 of the distal end portion 138. The angled inward section 140, along with the overall shape of the loading basket 108, allows the stent 114 to be secured within the loading basket 108 and prevents the stent 114 from unwanted shifting on the inner elongated member 102 during shipping and the stent loading process. Embodiments of the loading basket 108 may have at least one of the features described herein or any combination of the features described herein.

In some embodiments, there is an angle $\theta_1$ between the first section 139 and the second section 140. The smaller the angle $\theta_1$, the steeper the slope of the distal loop end 140, which allows for better grasping of the stent 114 within the loading basket 108. In some embodiments, the angle $\theta_1$ is between about 90 degrees and about 145 degrees. In some embodiment, the angle $\theta_1$ is between about 125 degrees and 135 degrees. In one embodiment, the angle $\theta_1$ is 130 degrees.

In some embodiments, there is an angle $\theta_2$ between the body portion 134 and the distal transition portion 136. The smaller the angle $\theta_2$, the steeper the slope of the distal transition portion 136, which allows for better grasp of the stent 114 within the loading basket 108. In some embodiments, the angle $\theta_2$ is between about 125 degrees and 135 degrees. In one embodiment, the angle $\theta_2$ is 130 degrees.

In some embodiments, there is an angle $\theta_3$ between the body portion 134 and the proximal transition portion 132. In some embodiments, the angle $\theta_3$ is between about 125 degrees and 135 degrees. In one embodiment, the angle $\theta_3$ is 130 degrees.

In at least one embodiment, $\theta_1$ is less than $\theta_2$. In at least one embodiment, $\theta_1$ is equal to $\theta_2$. In a preferred embodiment, the angle $\theta_2$ is 130 degrees. In at least one embodiment, $\theta_2$ is equal to $\theta_3$. In some embodiments, $\theta_1$ determined by stent geometry. In some embodiments, $\theta_2$ determined by stent geometry. In some embodiments, $\theta_3$ is determined by stent geometry. In some embodiments, all of the angles described herein correspond to angles of the stent; in some embodiments, all of the angles described herein do not correspond to angles of the stent.

In some embodiments, the proximal end portion 130 has a first diameter $D_1$, the body portion 134 has a second diameter $D_2$, and the distal end portion 138 has a third diameter $D_3$. In at least one embodiment, the diameter of the body portion $D_2$ is greater than the diameter of the distal end portion $D_3$, and the diameter of the distal end portion $D_3$ is greater than the diameter of the proximal end portion $D_1$. In at least one embodiment, the proximal transition portion 132 has a diameter that gradually increases from $D_1$ to $D_2$ from proximal end to distal end. In at least one embodiment, the distal transition portion 136 has a diameter that gradually decreases from $D_2$ to $D_3$ from proximal end to distal end. In at least one embodiment, the second section 140 of the distal end portion 138 has a diameter $D_4$ at distal end 112 is less than $D_3$. In at least one embodiment, the diameter $D_4$ is between about 70% and about 80% of the diameter $D_3$.

In some embodiments, the loading basket 108 is sized appropriately to the size of the stent 114 to be loaded into the loading basket. In at least one embodiment, $D_2$ is about 8 mm greater than a nominal diameter of the stent 114. In at least one embodiment, $D_3$ is about 1.5 mm greater than the nominal diameter of the stent 114. In at least one embodiment, $D_4$ is less than the nominal diameter of the stent 114. In at least one embodiment, $D_4$ is about 4.5 mm less than the nominal diameter of the stent 114. In at least one embodiment, the nominal diameter of the stent is the diameter at the body portion 124 shown in FIG. 1.

In at least one embodiment, the proximal end portion 130 has an axial length equal to or greater than the total of the axial lengths of the proximal transition portion 132, the body portion 134, the distal transition portion 136, and the distal end portion 138. The overall length of the basket 108 should be minimized because it affects the overall length of the delivery system.

The loading basket can be laser cut from a material or can be braided, twisted, knotted, knitted, woven, braided, bent, twisted, knotted, laser cut, molded, tied, and/or wrapped from one or several filaments into a desired configuration. In some embodiments, the loading basket can comprise mono-filament or multiple filament wires of any cross-section, including but not limited to round and rectangular. In some embodiments, the filament wires can be substantially flat. In at least one embodiment, the loading basket 108 is braided from a mono-filament of a variety of biocompatible materials such as polyethylene terephthalate (PET), other polymeric materials, and metals. In some embodiments, the loading basket can be comprised of shape memory alloys such as nitinol. The braiding process will be discussed further below.

FIG. 3 shows an embodiment of the loading basket 108. In this embodiment, the loading basket 108 further comprises a gripper feature 142 between the distal transition portion 136 and the distal end portion 138. The gripper feature 142 has a diameter $D_5$ that is less than the diameter $D_3$ of the first section 139 of the distal end portion 138. In at least one embodiment, $D_5$ is less than the nominal diameter of the stent 114. In at least one embodiment, $D_5$ is about 1.5 mm less than the nominal diameter of the stent 114. The smaller diameter and location of the gripper feature 142 increases the loading basket's ability to retain the stent.

Although FIG. 3 shows the loading basket 108 with both the angled inward second section 140 and the gripper feature 142, in some embodiments where the loading basket 108 is provided with the gripper feature 142, the second section 140 is not angled toward the longitudinal axis 113 relative to the first section 139 of the distal end portion 138 (in other words, the distal end portion 138 has a constant diameter along its axial length).

Figure 4:
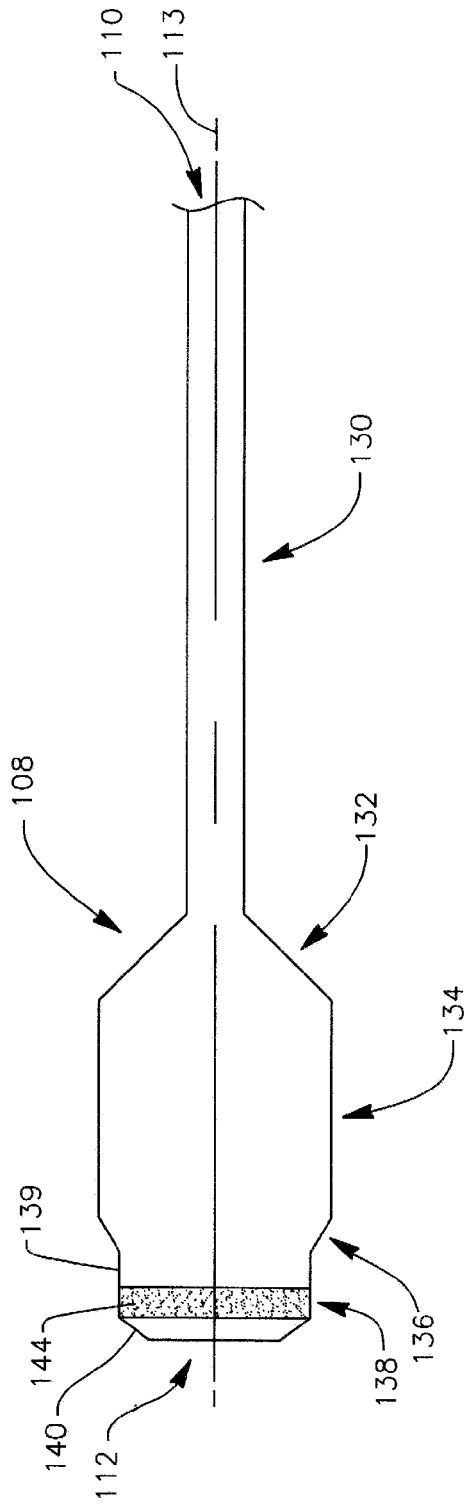
FIG. 4 shows a cross-sectional view of an embodiment of the loading basket of the present invention.

FIG. 4 shows an embodiment of the loading basket 108. In this embodiment, the loading basket 108 has at least one coating band 144 at the distal end portion 138. The coating band 144 extends around at least a portion of the circumference of the loading basket at the distal end portion 138. In some embodiments, the coating band 144 covers the second section 140. In some embodiments, the coating band 144 extends proximally from the distal end of the loading basket along a portion of the length of the second section 140. In some embodiments, the coating band 144 covers a portion of the first section 139. In some embodiments, the coating band 144 covers the entire distal end portion 138. The at least one coating band 108 may have any useful thickness, ranging from a nominally thin coating to a significantly thicker coating. In at least one embodiment, the coating band 144 can have a thickness that is less than a diameter of the filament wire used to form the loading basket 108. In at least one embodiment, the coating band 144 can have a thickness that is greater than a diameter of the filament wire used to form the loading basket 108.

In at least one embodiment, the coating band 144 comprises silicone. In at least one embodiment, the coating band 144 comprises a therapeutic agent. The therapeutic agent may be a drug or other pharmaceutical product such as non-genetic agents, genetic agents, cellular material, etc. In at least one embodiment, the therapeutic agent includes a polymer agent. The polymer agent may be a polystyrene-polyisobutylene-polystyrene triblock copolymer (SIBS), polyethylene oxide, silicone rubber and/or any other suitable substrate.

FIG. 5 shows an embodiment of the loading basket 108. In this embodiment, the loading basket 108 has a suture 146 that is woven into the braided surface of the loading basket 108 at the second section 140. In at least one embodiment, the suture 146 is woven at or substantially near the distal end 112. In at least one embodiment, the suture 146 is woven through the braided surface of the loading basket. In at least one embodiment, the suture 146 is woven through the end loops 141. The suture 146 can also be placed at other locations of the loading basket 108. By tightening the suture 146, the diameter of the loading basket 108 at the location of the suture 146 can be further restricted in order to retain the stent 114 in the loading basket 108.

In at least one embodiment, the gripping capability of the loading basket 108 can be positively effected by the coating band, the suture, and/or a restricting band disposed about the loading basket at a desired location on the basket. In one embodiment, the restricting band comprises an elastic filament.

FIG. 6 shows an embodiment of the loading basket 108. In this embodiment, the loading basket 108 has only the proximal end portion, the proximal transition portion 132, the body portion 134, and the distal end portion 138 that is angled inward towards the longitudinal axis 113.

In at least one embodiment, the inner surface of the loading basket 108 can be designed to increase or decrease surface contact with the stent. For example, additional coating bands can be used or the inner surface of the loading basket can have ridges or ribs to aid in gripping the stent in the loaded state.

It is within the scope of the present invention that any of the features and elements shown in the embodiments shown in FIGS. 2-6 or otherwise described above can be combined into an embodiment of the loading basket 108.

As discussed previously above, the loading basket 108 can be braided from a monofilament such as polyethylene terephthalate (PET) and other similar materials. In some embodiments, loading basket 108 is braided on a mandrel assembly 200, such as the mandrels shown in FIGS. 7-9.

FIG. 7 shows a perspective view of the mandrel assembly 200, which comprises a mandrel 202 having a proximal end 204 and a distal end 206, a hook end assembly 208, a mandrel shaft 210, a removable tube support 212, and a removable tube 214. In at least one embodiment, the mandrel 202 is attached to the mandrel shaft 210, which is used in conjunction with a braiding machine, such as the Herzog 36 carrier finite braider and other similar braiding machines. Braiding the loading basket 108 may also be accomplished by hand.

The mandrel 202 has a distinctive shape that corresponds to the desired shape of the finished loading basket 108. This shape will be further discussed with respect to FIGS. 8 and 9. The hook end assembly 208 can be removably engaged with the mandrel 202 near the distal end 206 of the mandrel 202. The hook end assembly 208 is used to form the distal loop end portion 138 (including the loops 141) of the loading basket 108. The hook end assembly 208 has a plurality of hooks 209. In some embodiments, embodiment, a first hook 209a is offset from a circumferentially adjacent second hook 209b. In at least one embodiment, the hook end assembly 208 has a first row of hooks and a second row of hooks, wherein, the second row of hooks are axially and radially offset from the first row of hooks. Although FIG. 7 shows the hook end assembly 208 with two rows of hooks, the hook assembly can have less than two rows of hooks or more than two rows of hooks. The hooks can also be tabs, pins, holes, slots, projections and other similar devices to help retain the filament during braiding.

The tube 214 is removably engaged with the mandrel shaft 204 and the mandrel 202. In some embodiments, the mandrel assembly 200 further comprises a tube support 212, which has a larger diameter than a diameter of the mandrel shaft 210. In at least one embodiment, the tube support 212 has a smaller diameter than the tube 214. In some embodiments, the outer surface of the tube support 212 contacts an inner surface of the removable tube 214. In at least one embodiment, an end of the tube 214 abuts the proximal end 204 of the mandrel 202. In at least one embodiment, the tube 214 has the same diameter as the proximal end 204 of the mandrel 202.

FIG. 8 shows a cross-sectional view of an embodiment of the mandrel 202 used to form the loading basket 108 of at least the embodiment shown in FIG. 2. Mandrel 202 has a proximal end portion 215, a proximal transition portion 216, a body portion 218, a distal transition portion 220, and a distal end portion 222 that substantially correlate to the desired shape of the proximal end portion 130, the proximal transition portion 132, the body portion 134, the distal transition portion 136, and the distal end portion 138 of the loading basket 108, respectively. In at least one embodiment, the mandrel 202 has the same diameters and angles as discussed above with respect to at least FIG. 2.

At least in the embodiment shown in FIG. 8, mandrel 202 also has a distal shaft 224 that extends distally from the distal end portion 222. Distal shaft 224 has a diameter that is less than the diameter of the distal end portion 222. In at least one embodiment, the distal shaft 224 has a diameter that is greater than the diameter of the proximal end portion 214. Referring to FIGS. 7 and 8, the hook end assembly 208 has a tubular configuration such that an inner surface of the hook end assembly engages with the outer surface of the distal shaft 224. In at least one embodiment, the hook end assembly 208 also abuts the distal end portion 222.

Figure 9:
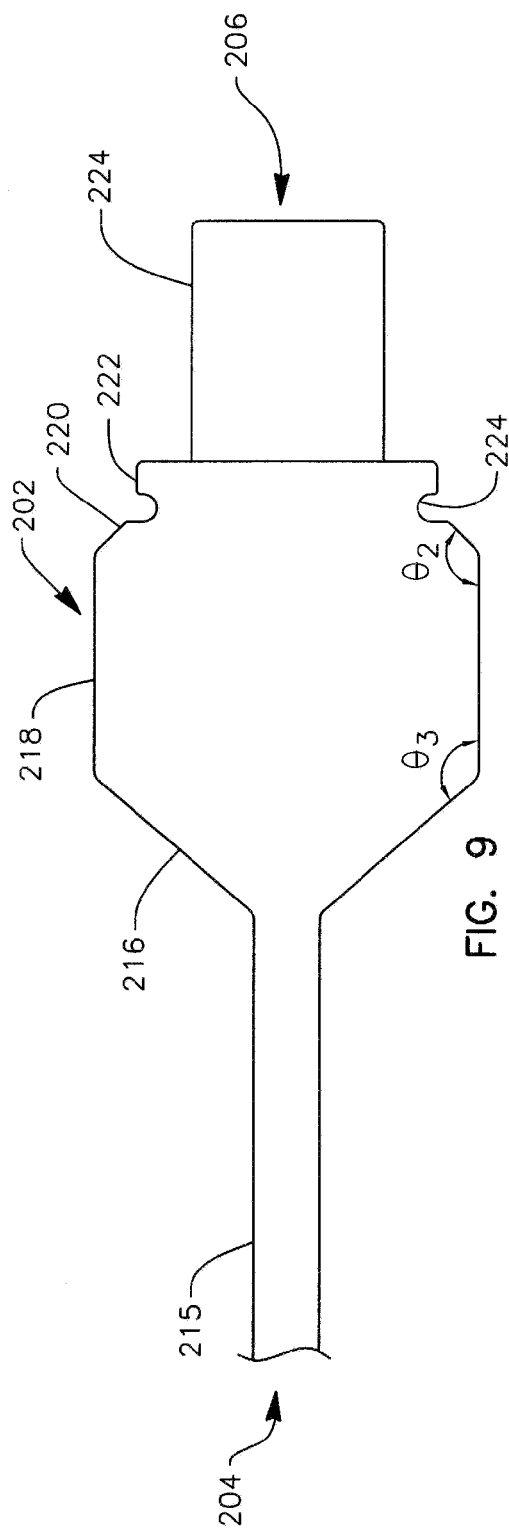
FIG. 9 shows a cross-sectional view of an embodiment of the mandrel.

FIG. 9 shows a cross-sectional view of an embodiment of the mandrel 202. In this embodiment, the mandrel 202 can be used to form a loading basket 108 having the gripper feature 142, which is shown in FIG. 3. In at least this embodiment, the mandrel 202 further comprises a gripping region 226 between the distal transition portion 220 and the distal end portion 222. In at least one embodiment, the proximal end portion 214, a proximal transition portion 216, a body portion 218, a distal transition portion 220, a distal end portion 222 of the mandrel 202 substantially correlate to the desired shape of the proximal end portion 130, a proximal transition portion 132, a body portion 134, a distal transition portion 136, and a distal end portion 138 of the loading basket 108. Angles $\theta_2$ and $\theta_3$ have the same magnitude as angles $\theta_2$ and $\theta_3$ of the loading basket shown at least in FIG. 2.

Figure 10A:
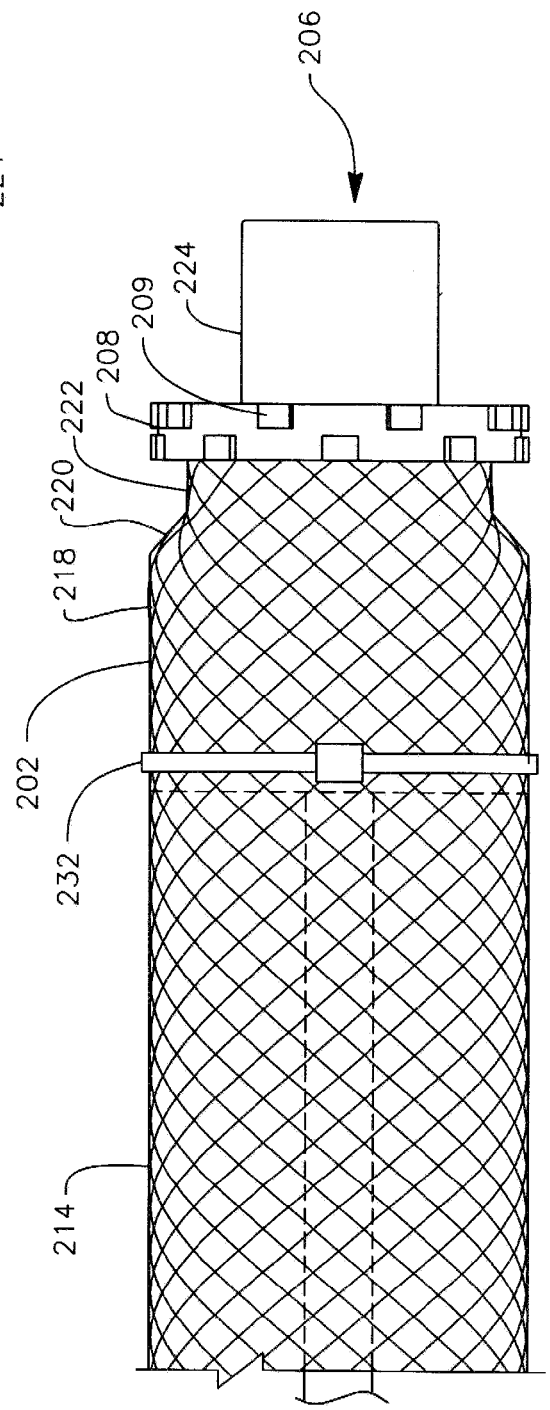
FIGS. 10A-10D show the method of forming the loading basket on the mandrel.

FIGS. 10A-10D illustrate a braiding process used to create the loading basket 108. FIG. 10A shows the loading basket 108 braided on the mandrel assembly 200. The monofilament 230 is helically wrapped distally from the proximal end 204 of mandrel 202 along the entire length of the mandrel 202 towards the distal end 206. Once the monofilament reaches the distal end 206 of the mandrel 202, the monofilament 230 is then wrapped around one of the hooks 209 of the hook end assembly 208 to form one loop 141 at the distal end 112 of the loading basket. The monofilament 230 is then helically wrapped proximally from the distal end 206 of the mandrel 202 along the entire length of the mandrel 202 back toward the proximal end 204 of the mandrel 202. The process is repeated until the surface 111 is completely formed.

In at least one embodiment, a retaining mechanism, such as cable tie 232, is used to ensure that the braided portion contacts the mandrel 202 in a desired fashion so that the finished basket has the proper shape. This prevents the braided portion from deviating away from the mandrel 202 during the manufacturing process. In at least one embodiment, the retaining mechanism 232 is placed around the circumference of the body portion 218 of the mandrel 202. In some embodiments, a retaining mechanism 232 can be placed around the mandrel assembly at a proximal end of the removal tube 214.

Figure 10B:
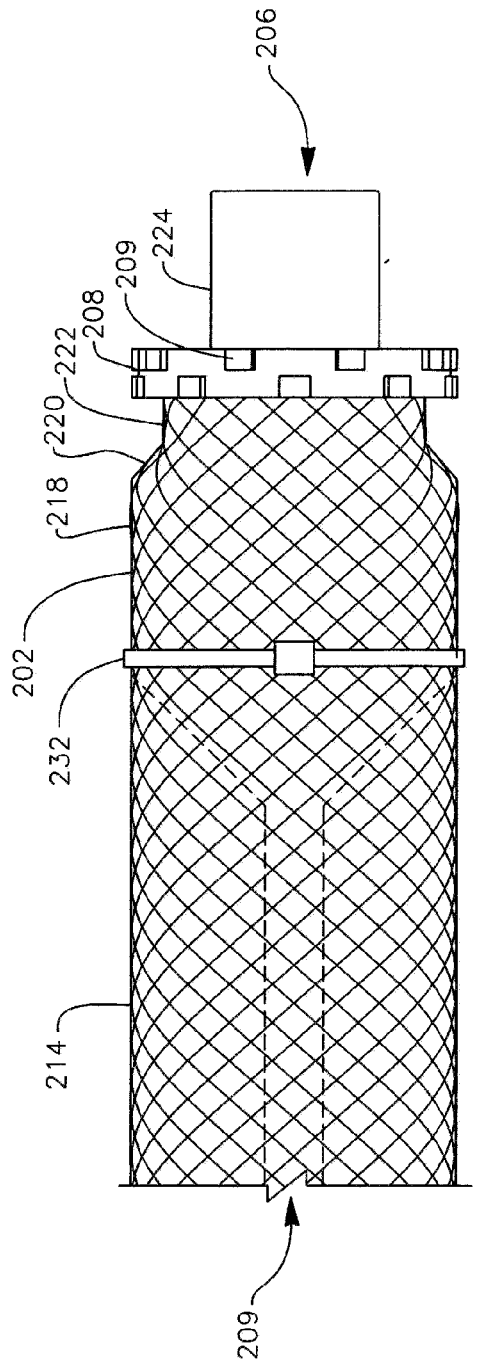
Figure 10C:
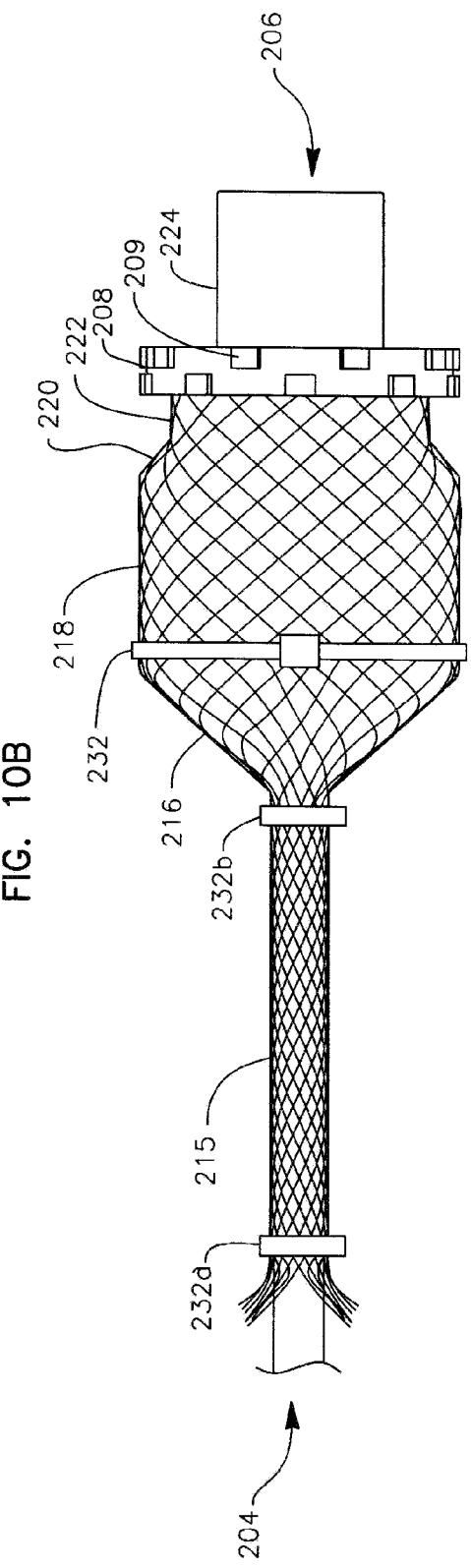

Once the braiding is completed, the mandrel assembly 200 is removed from the braiding machine. The tube 214, including tube support 212, is removed from the mandrel assembly 202 as shown in FIG. 10B. Once the tube 214 is removed, additional retaining mechanisms 232 can be used to tighten the braided surface 111 about the proximal end portion 215 to form the proximal end portion 130 of the loading basket. FIG. 10C shows a first retaining mechanism 232a positioned at the desired proximal end 116 of the loading basket 108 and a second retaining mechanism 232b at the location where the proximal end portion 215 and the proximal transition portion 216 meet.

Figure 10D:
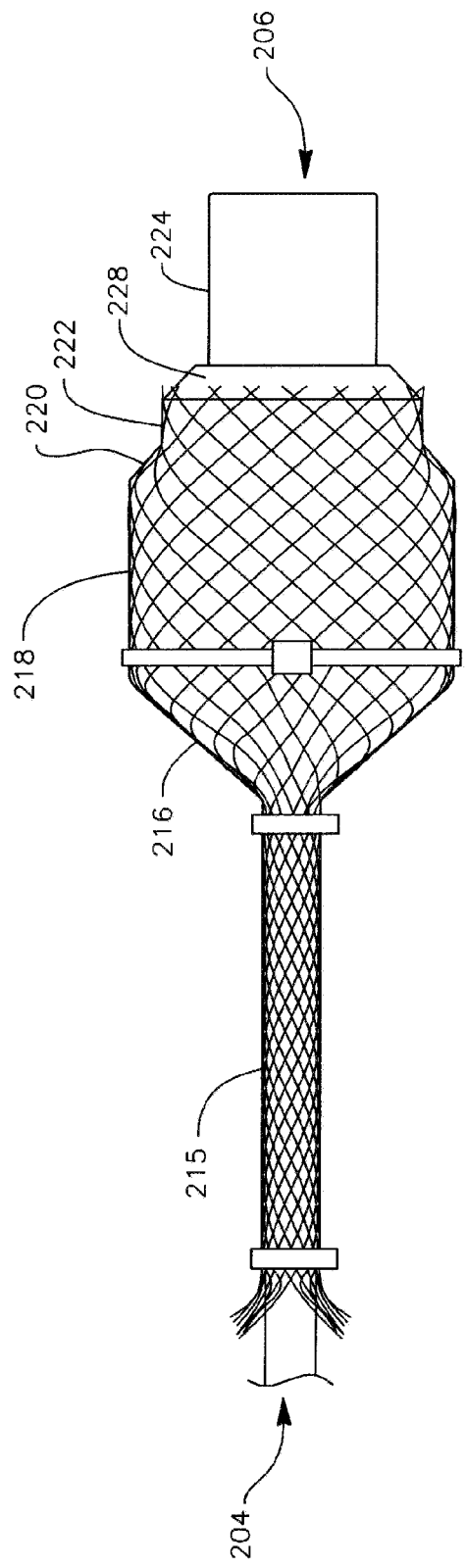

As shown in FIG. 10D, the hook end assembly 208 is then removed from mandrel assembly 200. A forming ring 228 is then placed over the distal shaft 224 such that one end of the forming ring abuts the distal end portion 222 of the mandrel 202. The forming ring 228 is used to form the loading basket distal loop end diameter. In some embodiments, a suture is used to tie the distal loop end onto the forming ring to create the appropriate angle for the distal loop end of the loading basket. In some embodiments, the forming ring 228 has a tapered outer diameter of the desired angle between the first section 139 and the second section 140 of the distal end section 138. In such embodiments, the end of the forming ring with the largest outer diameter abuts the distal end portion 222 of the mandrel 202.

In embodiments where a gripper feature 142 is desired and the mandrel 202 has a gripping region 226, a suture or other wire is wrapped around the circumference of the mandrel at the gripping region and tightened such that the braided surface substantially conforms to the shape of the mandrel.

Finally, the mandrel may be heat set at a standard temperature to form the loading basket 108 into shape, and the finished loading basket 108 is then removed from the mandrel assembly when annealing is complete.

Figure 11A:
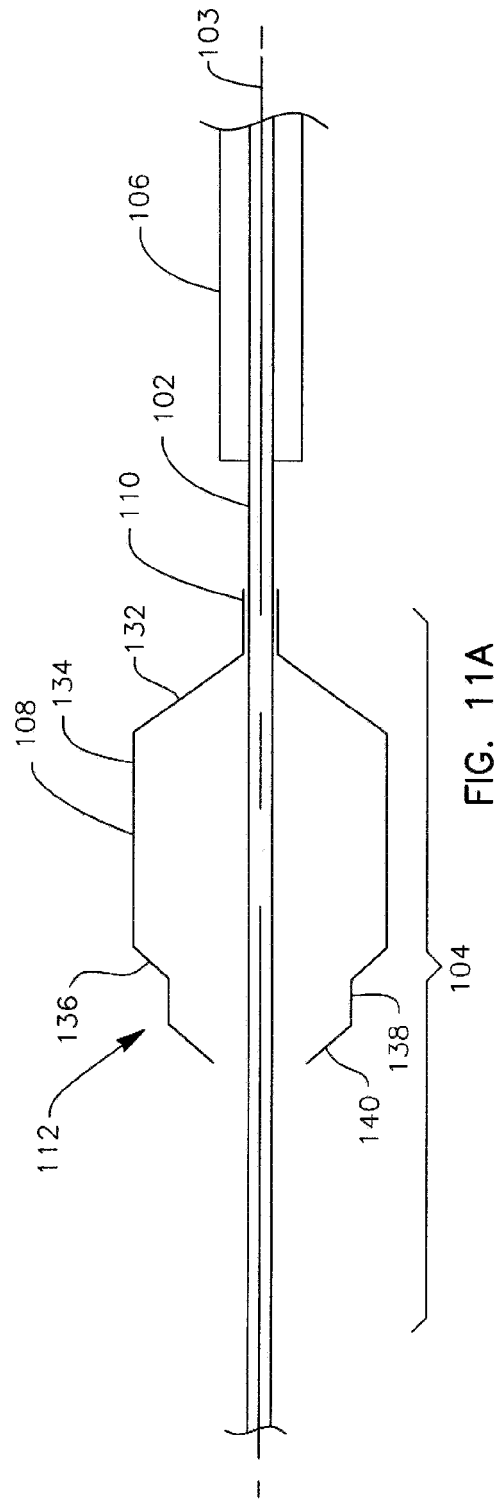
Figure 11D:
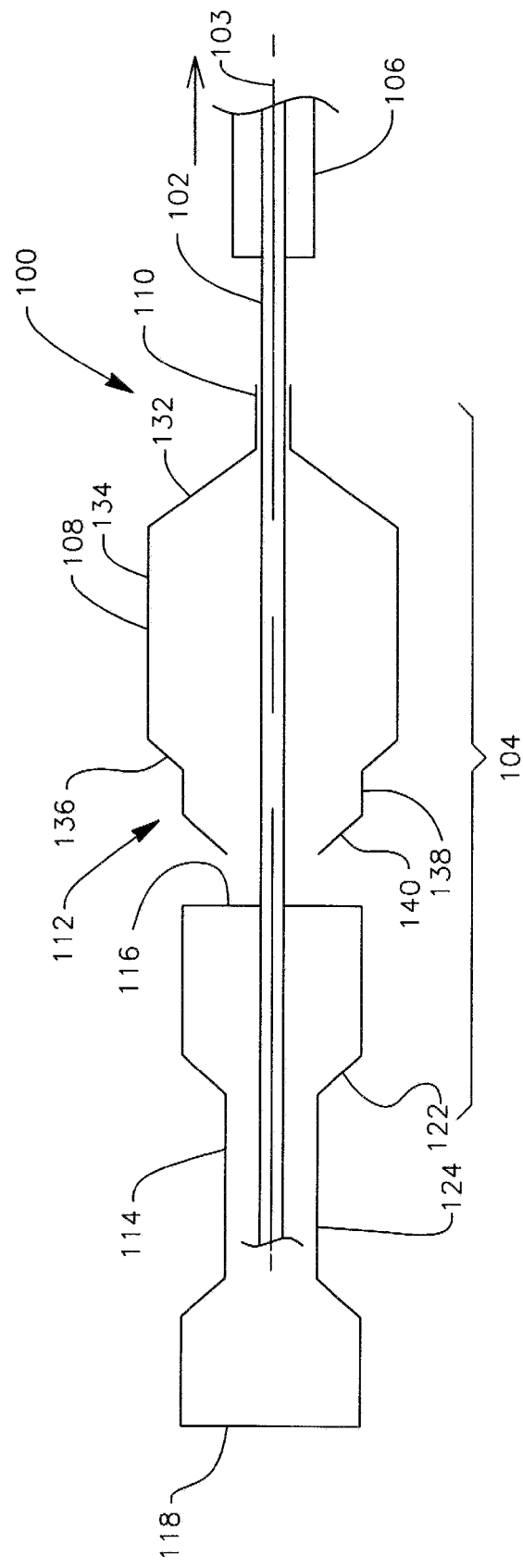

FIGS. 11A-11D illustrate a method used to load the stent onto the stent delivery system. FIG. 11A shows the stent delivery catheter assembly 100 with the proximal end 110 of the loading basket 108 attached to the intermediate tubular member 105. The loading basket 108 is fully expanded and ready to receive the stent 114.

As shown in FIG. 11B, the proximal end 116 of the stent 114 is inserted into the lumen 115 of the loading basket 108. In at least one embodiment, the stent 114 is coaxial with the intermediate tubular member 105. The outer surface of the stent 114 contacts the inner surface of the loading basket 108 at least at the second section 140 of the distal end portion 138. In some embodiments, the outer surface of the stent 114 contacts the inner surface of the loading basket 108 at the gripper feature 142 of the loading basket 108. In at least some embodiments where the stent 114 is a flared stent, the proximal end section 120 rests fully inside the body portion 134 of the loading basket 134. As shown in FIG. 11B, the distal end 118 of the stent 114 is free.

As shown in FIG. 11C, the outer sheath 106 is slid over both the loading basket 108 and the stent 114 such that both are radially compressed. The stent delivery system is advanced to a desired location in the bodily lumen. When the stent is being deployed, the intermediate tubular member 105 and the outer tubular member 106 are retracted to deploy the stent. The stent 114 radially expands within the lumen. The inner elongated member 102, the intermediate tubular member 105 (including the attached loading basket 108), and the outer tubular member 106 are all retracted, leaving the stent 114 at the desired location in the bodily lumen.

In any embodiment, the loading basket 108 may be elastic, compliant, non-compliant, or can be designed such that certain sections have various features and characteristics for expansion and flexibility.

In any embodiment, the inner surface of the loading basket 108 may have any number of features that interact with the stent 114 in order to improve contact between the loading basket 108 and the stent 114, including but not limited to ridges, ribs, bumps, coatings, surface abrasions or roughness, and other similar features. In some embodiments, the outer surface of the stent 114 may have any number of features that interact with the inner surface of the loading basket 108 in order to improve contact between the loading basket 108 and the stent 114, including but not limited to ridges, ribs, bumps, coatings, surface abrasions or roughness, and other similar features.

In some embodiments, the material of loading basket 108 may be chosen to improve the gripping capability of the loading basket 108 relative to the stent 114. In some embodiments, the material of loading basket 108 may be selected relative to the material used for the stent 114, and vice versa.

In some embodiments, the outer surface of the stent 114 may be provided with tacky coating that improves the contact of the loading basket 108 with the stent 114. In some embodiments, the inner surface of the loading basket 108 may be provided with tacky coating that improves the contact of the loading basket 108 with the stent 114.

In some embodiments, the stent and the loading basket may have an interlocking region that only serves to secure the stent, but has no effect on the stent performance. Examples of interlocking regions include but are not limited to an annular ridge on the stent that engages with an annular groove on the loading basket; an annular ridge on the stent that engages with an annular groove on the loading basket; hook and loop connections, and other similar interlocking mechanisms. Any number of features may be provided on the loading basket 108, the stent 114, or both to improve the loading basket's grip on the stent.

In one embodiment, a mandrel assembly for manufacturing the loading basket described above is provided. The mandrel assembly comprises a mandrel having a proximal end portion; a proximal transition portion; a proximal body portion; a distal transition portion; a distal body portion; and a distal end portion. In at least one embodiment, the mandrel assembly further comprises a removable hook end assembly comprising a ring with a plurality of hooks on an outer surface of the ring. In at least one embodiment, the mandrel assembly further comprises a removable tube having a diameter equivalent to a diameter of the proximal body portion of the mandrel. In at least one embodiment, the mandrel further comprises a gripping region between the distal transition portion and the distal end portion.

In at least one embodiment, a method of manufacturing a loading basket is provided. The method comprises braiding the loading basket using a braiding machine having a mandrel assembly, the mandrel assembly comprising a mandrel, a removable tube, and a removable hook end assembly; wherein the mandrel has a proximal end portion; a proximal transition portion; a proximal body portion; a distal transition portion; a distal body portion; and a distal end portion, wherein the removable tube has a diameter equivalent to a diameter of the proximal body portion of the mandrel, wherein the removable tube abuts the body portion of the mandrel and extends proximally therefrom, wherein the removable hook end assembly abuts the distal end portion. In at least one embodiment, the method further comprises removing the mandrel assembly from the braiding machine after the loading basket is braided. In at least one embodiment, the method further comprises removing the removable tube from the mandrel assembly. In at least one embodiment, the method further comprises. positioning at least two retaining mechanisms about the braided loading basket and mandrel assembly; wherein a first retaining mechanism at a desired proximal end of the loading basket and a second retaining mechanism where the proximal end portion and the proximal transition portion meet. In at least one embodiment, the method further comprises removing the hook end assembly from the mandrel assembly. In at least one embodiment, the method further comprises inserting a forming ring having a tapered outer diameter at a distal end of the distal end portion, the forming ring abutting the distal end portion. In at least one embodiment, the method further comprises applying heat. In at least one embodiment, the method further comprises removing the forming ring and the mandrel assembly from the loading basket.

This completes the description of the preferred and alternate embodiments of the invention. Those skilled in the art may recognize other equivalents to the specific embodiment described herein, the equivalents of which are intended to be encompassed by the claims attached hereto.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to."

The invention claimed is:

1. An expandable stent loading basket, the basket having a proximal end, a distal end, and a surface, the basket comprising:
   a proximal end portion at the proximal end, the proximal end portion having a diameter;
   a proximal body portion connected to the proximal end portion, the proximal body portion having a diameter;

a distal transition portion connected to the proximal body portion;

a distal body portion connected to the distal transition portion, the distal body portion having a diameter;

a gripper region between the distal transition portion and the distal body portion, the gripper region having a diameter smaller than the diameter of the distal body portion and smaller than a diameter of the distal transition portion; and a distal end portion connected to the distal body portion and forming the distal end of the basket, wherein the distal end portion has a diameter that tapers from a diameter of the distal body portion to a diameter at the distal end of the basket, wherein the diameter at the distal end is less than the diameter of the distal body portion, the diameter at the distal end is greater than the diameter of the proximal end portion, the diameter of the proximal body portion is greater than the diameter of the distal body portion, and the diameter of the distal body portion is greater than the diameter of the proximal end portion;

wherein the basket is expandable from a radially compressed configuration to a radially expanded configuration.

2. The loading basket of claim 1, wherein at least a portion of the distal body portion has a coating band.

3. The loading basket of claim 1, further comprising a proximal transition portion between the proximal end portion and the proximal body portion.

4. The loading basket of claim 3, further comprising:
a first angle between the distal body portion and the distal end portion;
a second angle between the proximal body portion and the distal transition portion; and
a third angle between the proximal body portion and the proximal transition portion;
wherein the first angle is between about 90° and about 145°; the second angle is between about 125° and 135°; and the third angle is between about 125° and 135°.

5. The loading basket of claim 4, wherein the second angle is equal to the first angle and the third angle is equal to the second angle.

6. The loading basket of claim 1, wherein the distal end portion has a plurality of loops that define the distal end of the loading basket.

7. The loading basket of claim 1, wherein the surface is braided, and a filament is woven through the braided surface around a circumference of the loading basket at the distal end.

8. The loading basket of claim 1, wherein the proximal end portion has an axial length greater than the proximal body portion, the distal transition portion, the distal body portion, and the distal end portion combined.

9. The loading basket of claim 1, wherein the diameter at the distal end of the loading basket is between about 70% and about 80% the diameter of the distal body portion.

10. The loading basket of claim 1, further comprising a suture woven into the distal end portion.

11. The loading basket of claim 10, wherein the distal end region comprises end loops and the suture is woven into the end loops of the distal end portion.

12. The loading basket of claim 1, wherein the loading basket comprises a single monofilament.

13. The loading basket of claim 1, wherein the loading basket forms a part of a stent delivery system comprising:

a first member having a stent loading region;
a second member slidably engaged with the first member, the second member having the loading basket attached thereto.

14. The loading basket of claim 13, the stent delivery system further comprising a stent having a proximal end, a proximal flared section, a body section, a distal end, and a wall defining a lumen, wherein:
the proximal flared section of the stent is deposited into the proximal body portion of the loading basket and the body section extending therefrom,
the lumen of the stent is disposed around the stent loading region of the first member, and
the distal end portion or the gripper region of the loading basket contacts an outer surface of the stent.

15. The loading basket of claim 14, wherein the diameter of the distal end of the loading basket is less than a diameter of the body section of the stent.

16. The loading basket of claim 14, wherein the gripper region has a diameter less than a nominal diameter of the stent.

17. The loading basket of claim 13, wherein the stent delivery system further comprises a third member slidably engaged with the second member, the first member being coaxial with the second member which is coaxial with the third member.

18. An expandable stent loading basket, the basket having a distal end, an outer surface and an inner surface, the basket comprising:
a proximal end portion extending distally from the proximal end, the proximal end portion having a first inner diameter;
a proximal body portion extending distally from the proximal end portion, the proximal body portion having a second inner diameter;
a tapered distal transition portion extending distally from the proximal body portion;
a distal body portion extending distally from the distal transition portion, the distal body portion having a third inner diameter, the third inner diameter being greater than the first inner diameter and less than the second inner diameter, the tapered distal transition portion tapering, in a distal direction, from the second inner diameter down to the third inner diameter; and
a tapered distal end portion extending distally from the distal body portion to the distal end, the distal end having a fourth inner diameter greater than the first inner diameter and less than the third inner diameter, the tapered distal end portion tapering, in a distal direction, from the third inner diameter down to the fourth inner diameter;
wherein the basket is expandable from a radially compressed configuration to a radially expanded configuration.

19. The loading basket of claim 18, wherein the second inner diameter is substantially constant along the proximal body portion from the proximal end portion to the tapered distal transition portion, and the third inner diameter is substantially constant along the distal body portion from the tapered distal transition portion to the tapered distal end portion.

20. The loading basket of claim 18, wherein a length of the proximal body portion is greater than a length of the distal body portion and the tapered distal end portion combined.

* * * * *